United States Patent [19]

Engle

[11] 4,148,217

[45] Apr. 10, 1979

[54] EVALUATING SURFACTANTS

[75] Inventor: Charles J. Engle, Bartlesville, Okla.

[73] Assignee: Phillips Petroleum Company, Bartlesville, Okla.

[21] Appl. No.: 847,345

[22] Filed: Oct. 31, 1977

[51] Int. Cl.² ........................................... G01N 15/00
[52] U.S. Cl. ........................................ 73/60.1; 73/38
[58] Field of Search ................. 73/60.1, 61.1 R, 61.4, 73/38

[56] References Cited

U.S. PATENT DOCUMENTS

| | | | |
|---|---|---|---|
| 2,498,198 | 2/1950 | Beeson | 73/38 |
| 2,733,595 | 2/1956 | Twining | 73/61.4 X |
| 3,073,149 | 1/1963 | Mongan | 73/38 |

Primary Examiner—Richard C. Queisser
Assistant Examiner—Joseph W. Roskos

[57] ABSTRACT

A method for evaluating foam-producing surfactants by measuring the resistance to the flow of a gas, for example, nitrogen, through a standard sand pack containing a solution of the surfactant. The resistance is also measured when the sand pack contains water, thereby allowing the surfactant solution's resistance factor to be determined. The resistance factor for a surfactant solution is defined as the ratio of the maximum pressure drop observed across the sand pack when the pore space was filled with the surfactant foam to the maximum pressure drop when the sand pack was filled with water and was being displaced by a gas flow.

12 Claims, 5 Drawing Figures

EVALUATING SURFACTANTS

BACKGROUND OF THE INVENTION

This invention relates to a method for evaluating a surfactant. In another aspect, it relates to obtaining a quantitative measure of foam quality of form-producing surfactants. In another aspect, it relates to a test method for selecting suitable surfactants for use in steam-surfactant floods wherein foam is formed in the presence of steam. In another aspect, it relates to a method of evaluating such surfactants in the presence of a gas. In still another aspect, the invention relates to a method of evaluating foam-producing surfactants by measuring the resistance of a flow of gas through a sand pack containing first water and then the surfactant solution. In another aspect, it relates to a method of evaluating foam-producing surfactants by measuring the pressure drop while passing a gas through the sand pack containing water and then again measuring while passing a gas through the sand pack containing the surfactant solution. In yet another aspect, this invention relates to a method of evaluating foam-producing surfactants by measuring the pressure drop across the sand pack during continuous flow of both gas and water and then during continuous flow of both gas and surfactant solution. In still another aspect, it relates to testing the thermal stability of a surfactant by applying the test method both before and after a surfactant solution has been thermally aged.

Field tests have shown that significant amounts of incremental oil can be produced profitably using the steam-foam diversion process. In the steam-foam diversion process, the foaming surfactant is injected simultaneously with steam. A foam is produced with the steam in situ; and, consequently, the process is normally referred to as the steam-foam process. While the steam-foam diversion process has experienced good success in the field, only limited laboratory screening has been applied to select the best surfactant for the process.

The thermal stability of the surfactant is an important factor in selecting a surfactant for field applications. Many surfactants lose their ability to produce effective foams after a few hours at temperatures of about 325° F. Nonionic surfactants have better thermal stability than anionic and possibly cationic surfactants, and, for that viewpoint, are preferred for field applications. However, if a screening test was available, one could accurately pick the best surfactant without using a speculative rule considering only one aspect of the many aspects that should be considered in choosing a surfactant.

Laboratory screening tests, therefore, would allow one to choose the best thermally stable surfactant with good foaming ability in order to provide the optimum diversion of steam from the "steamed-out" zones to less permeable zones which have not been exposed to much steam. The heating of these zones would result in improved oil recovery in cyclic-steam operations in heavy oil reservoirs. The choosing of a surfactant, therefore, is important to the efficiency and proficiency of the recovery process, and an accurate screening test used in choosing the best surfactant would be a very helpful and important tool in the overall recovery process.

U.S. Pat. No. 3,785,437 describes a method for determining the ability of polymers to shut off water in sand cores by determining the residual resistance factor (RRF). The residual resistance factor is defined as the initial permeability to brine divided by the final permeability to brine in the presence of gelled and entrapped polymer, and in the presence of residual oil saturation. The residual resistance factor to oil is defined as the initial oil mobility in the presence of connate water divided by the final oil mobility following the polymer treatment. The patentees, therefore, evaluate polymers in water floods. The tests are for the use of different liquid phases, e.g., thickened water and a driving fluid. However, the steam-foam diversion process utilizes steam, primarily a gaseous vapor, not a liquid. A screening method, therefore, making measurements on surfactants in the presence of a gas, e.g., nitrogen, would be more appropriate and more accurate in selecting the best surfactant for a steam-diversion process.

An object of the instant invention, therefore, is to provide for an accurate method of evaluating surfactants for a steam-diversion oil recovery process.

Another object is to allow one to change the concentration of a surfactant solution while testing the surfactant solution.

Another object is to provide such a method which simulates the presence of steam in an oil well.

Another object of the present invention is to provide for a more efficient and proficient steam-diversion oil recovery process through the selection of a proper surfactant.

Yet another object is to provide a method of determining the thermal stability as well as the foaming ability of a surfactant.

These and other objects, aspects, and the several advantages of this invention will be apparent to those skilled in the art upon a study of this disclosure, the drawings, and the appended claims.

SUMMARY OF THE INVENTION

According to the invention, a surfactant solution is evaluated as to foaming ability by measuring how well the foamed solution can stop the flow of gas through a sand pack as compared to water. This evaluation allows one to pick the best surfactant for use in secondary oil recovery processes, particularly those in which steam-surfactant floods are used. This can be done either by measuring the pressure drop across a sand pack during the displacement of water by a gas and then comparing it with the pressure drop across the sand pack during the displacement of a surfactant solution by the gas; or by comparing the pressure drop across a sand pack while continuously pumping both gas and water through the sand pack with the pressure drop when pumping both gas and surfactant solution through the sand pack.

The thermal stability of a surfactant solution can also be determined by the present invention by employing the methods of the present invention both before and after the surfactant solution has been thermally aged. Surfactant concentration and oil reservoir porosity are two other factors that can be considered by the present invention's test methods by changing the surfactant concentration and using a sand pack of that particular porosity of the actual oil reservoir. The ability to consider these factors allows one to choose accurately the best foaming surfactant for the oil recovery process.

DETAILED DESCRIPTION OF THE INVENTION

The present invention relates to a method for evaluating and selecting suitable surfactants for use in secondary recovery methods, particularly those in which steam-surfactant floods are used wherein foam is formed in the presence of steam.

The method of the present invention carries out the measurements on the surfactants in the presence of a gas which is used to create bubbles simulating steam. The simulation of the steam provides for a more accurate assessment of the surfactant when it is to be foamed in the presence of steam. The method is applicable, however, in evaluating the foaming ability of any foam-producing surfactant, whether to be used with steam or not.

The present invention evaluates foam-producing surfactants by determining what is called resistance factor. The pressure drop across a sand pack is measured while passing a gas, e.g., nitrogen, through the pack containing water and then again measured while passing the gas through the pack containing a surfactant solution. The ratio of the two pressure drops thus measured is the resistance factor of the surfactant solution. Since the foam produced by the surfactant solution reduces the fingering of injected steam and diverts the steam into less permeable areas of the reservoir, the resistance factor of the surfactant solution, as determined by the testing methods of the present invention, should provide a measure of the ability of the foam to divert steam into less permeable areas of the reservoir in an actual field application.

The gas used in the present invention can be any relatively inert gas suitable for such an application. Examples of such gases are nitrogen, carbon dioxide, carbon monoxide, methane, air, helium, and argon. Nitrogen is the preferred gas due to its inert character and ready availability.

In a specific embodiment of the present invention, water is first passed through the sand pack by itself, then a gas is passed through the sand pack by itself to displace the water and the pressure drop measured. A foam-producing surfactant solution is then passed through the pack itself followed by the passage of a gas causing the surfactant to foam. The pressure drop is then measured and the ratio of the maximum differential pressure observed during the foam flood divided by the maximum differential pressure during the gas-water flood gives the resistance factor for the surfactant solution. The resistance factor, thereby, provides a qualitative measure of foam quality.

In another specific embodiment of the present invention, the pressure drop is measured across the sand pack during a continuous flow of both water and gas and then again during the continuous flow of both the surfactant solution and gas. The resistance factor is determined accordingly by taking the ratio of the maximum differential pressure during the flow of surfactant and gas divided by the maximum differential pressure observed during the flow of water and gas.

Factors such as the thermal stability of the surfactant and surfactant concentration can also be measured and tested using the present invention. Surfactant concentration is tested by merely changing the concentration of the surfactant from test to test. Thermal stability of a particular surfactant solution is determined by measuring the resistance factor before and after the surfactant solution has been heated for a predetermined time. The length of time the surfactant solution is heated can be up to 100 hours or more, or whatever length of time is felt necessary to adequately determine the surfactant solution's thermal stability. It has been found, however, that heating the surfactant solution for a period of time in the range of 3-18 hours is adequate in giving a good indication of a surfactant solution's thermal stability. The temperature at which the surfactant solution is heated approximates that which exists in actual field applications. Such temperatures reach from 300°–500° F. (150°–260° C.).

The pressure of the gas used in the present invention need only be sufficient to displace the water from the sand pack. An initial gas pressure of about 50 to 200 psi is usually sufficient, but the pressure required will vary according to the ease of displacement from the sand pack.

The rate of flow of the water, gas, and surfactant solution when the surfactant solution is being evaluated using a continuous flow of gas and water and then gas and surfactant solution can be in the range of about 2 to 25 gallons per hour per square foot of sand pack cross-sectional area for the water and surfactant solution and 5 and 50 cubic feet per hour per square foot of sand pack cross-sectional area for the inert gas.

The permeability of the reservoir can also be taken into consideration in the testing of the surfactant solution by the present invention. The sand pack's permeability (as measured in Darcys; See U.S. Pat. No. 3,727,687, column 13) can approximate that of the oil reservoir in order to assure an evaluation for the proper environment. As well, different types of sand can be used.

The testing, measuring, and consideration of the effects of thermal aging, variance in surfactant concentration, and permeability can be applied successfully to surfactant solutions using both of the specific embodiments of the present invention. The testing and consideration of these factors through the use of the present invention will help in selecting the best available surfactant.

The present invention, therefore, allows one to evaluate the foaming ability of foam-producing surfactant solutions by determining the resistance factor of the surfactant solutions. Two specific embodiments of the present invention are the "displacement-type test" (as illustrated in Example I) and the "continuous flow-type test" (as illustrated in Example II). The present invention will be better understood through illustration by the following examples. The following examples are set forth as merely illustrations of the present invention and are not meant to be restrictive.

EXAMPLE I

The total of 38 different surfactants were evaluated in this example. The trade name, generic name, ionic type, and supplier of each surfactant are shown in Table I.

Figure 3:
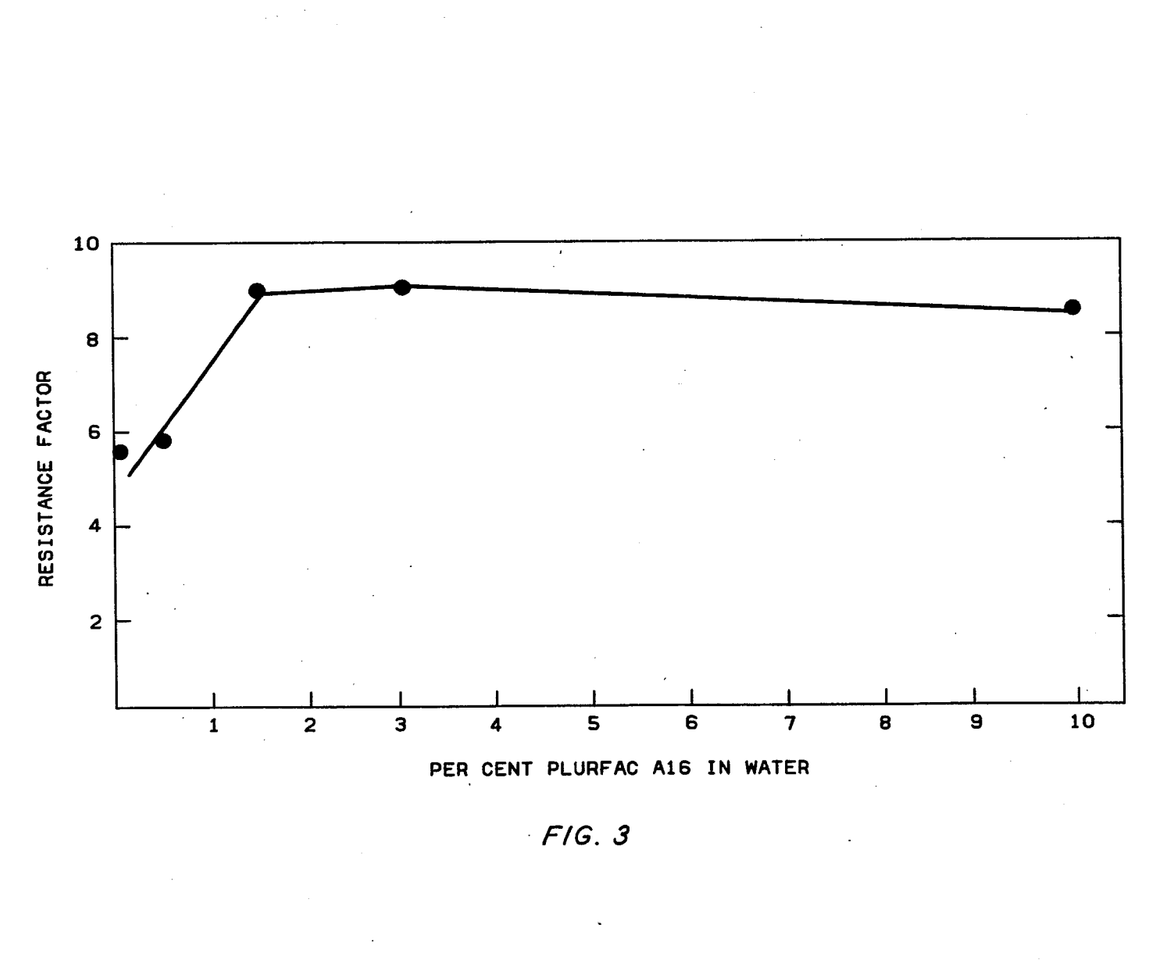
FIG. 3: Graph showing effect of surfactant concentration on resistance factor.

Surfactant solutions in concentrations up to 10 weight percent surfactant were prepared in Bartlesville, Okla. tap water. Solutions containing different concentrations of surfactants were used to establish the effect of concentration on foaming ability. However, as shown in FIG. 3, the resistance factor increases with surfactant concentration up to about 1.5 weight percent and is then essentially independent of concentration at higher surfactant concentrations. Therefore, as a result of this fact, all additional tests were made at surfactant concentrations of 3.0 percent.

Figure 2:
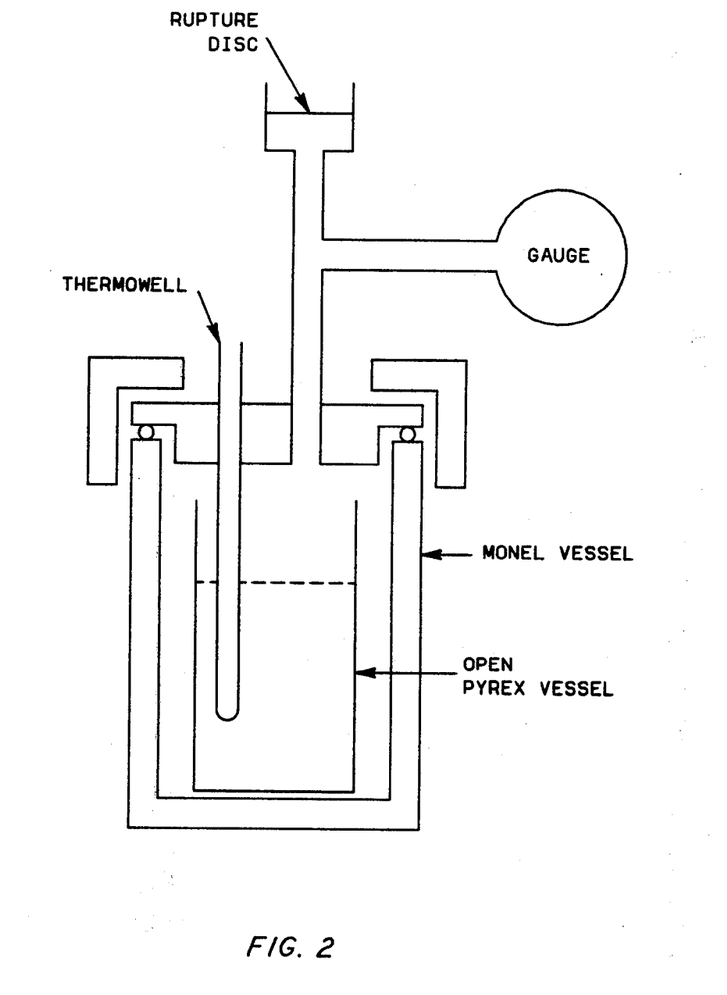
FIG. 2: Vessel for the thermal aging of test solutions.

The foaming potentials of some of the 3.0 percent surfactant solutions were also measured both before and after the solutions were thermally aged at temperatures approximating reservoir temperatures in actual field applications. The equipment used for thermally aging the surfactant solutions was essentially a glass-lined pressure vessel, shown schematically in FIG. 2. The vessel was rated at 2,000 psi at 600° F. and was equipped with a 3,000 psi pressure gauge and a 1,300 psi rupture disc. Any vessel, however, which would enable one to thermally age the surfactant solution for an extended period of time would be appropriate.

Figure 1:
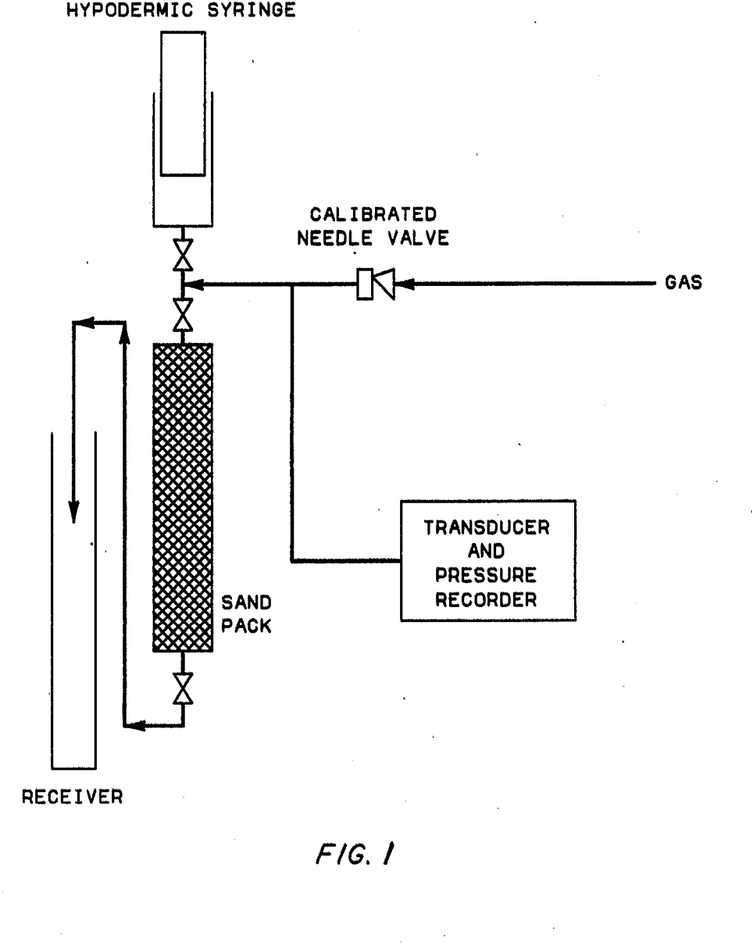
FIG. 1: Apparatus for measuring resistance factors.

The equipment used for the "displacement-type test" is shown schematically in FIG. 1. Any appropriate sand pack equipment can be used and the present invention should not be restricted to that used in this example. The equipment consisted of a nominal one-inch (2.7 cm) internal diameter schedule 40 steel pipe 11.5 inches (29.2 cm) long threaded at the ends and mounted in a vertical position. A horizontal position may be used, but a vertical position is preferred. The tube was equipped with stainless steel sand retaining screens, filled with Ottawa sand, and capped with steel reduced couplings having needle valves.

TEST PROCEDURE

The tube was filled with water, and nitrogen, e.g., from a 100 psi source, was introduced into the tap. Water was then displaced out the bottom by the nitrogen flow and the pressure drop across the sand pack during water displacement by the gas flood was measured with a capacitance-type transducer (e.g., Dynasciences Corporation, KP15 and Model D25 translator) and recorded on a strip chart recorder (e.g., Sargent Model SR).

Surfactant solutions (normally three pore volumes) were introduced into the top of the tube with a hypodermic syringe, displacing water out the bottom. The surfactant solution was pushed through the sand pack with nitrogen causing foam to be generated in situ, and the pressure drop across the sand pack was measured in the same manner as described above for the gas-water flood. The ratio of the maximum differential pressure observed during the foam flood divided by the maximum pressure during the gas-water flood which is the resistance factor provided a qualitative measure of foam quality.

The resistance factor of several surfactants was evaluated both before and after the surfactant solution had been thermally aged. The above procedure was first performed on the surfactant solution to determine its resistance factor at room temperature. Then the surfactant solution was placed in the thermal aging vessel (FIG. 2), sealed, and then heated at the desired temperature in a laboratory oven. The temperature of the test solution can be monitored continuously with an iron-constantan thermocouple sealed into the vessel. After heating for the predetermined time, the above "displacement-type test" procedure is again applied to the surfactant solution to determine the effect of the thermal aging on the resistance factor of the surfactant solution.

Results

The resistance factor, defined as the ratio of the maximum pressure drop observed across the sand pack when the pore space was filled with the surfactant foam to the maximum pressure drop when the pack was filled with water and gas and was being displaced by nitrogen, for each of the 38 surfactants (three percent by weight solutions) were measured and tested in Table II in order of descending resistance factor.

Incremental oil produced as a result of steam-foam injection in cyclic steaming operations is believed to result from improved sweep efficiency of the steam. Basically, the foam tends to reduce fingering and diverts steam into less permeable areas of the reservoir. Consequently, the resistance factor of the surfactant solution, as determined by testing in a sand pack, provides a measure of the ability of the foam to divert steam into less permeable areas of the reservoir in an actual field application. The surfactant with the largest resistance factor, therefore, would divert the steam with the greatest efficiency.

Figure 4:
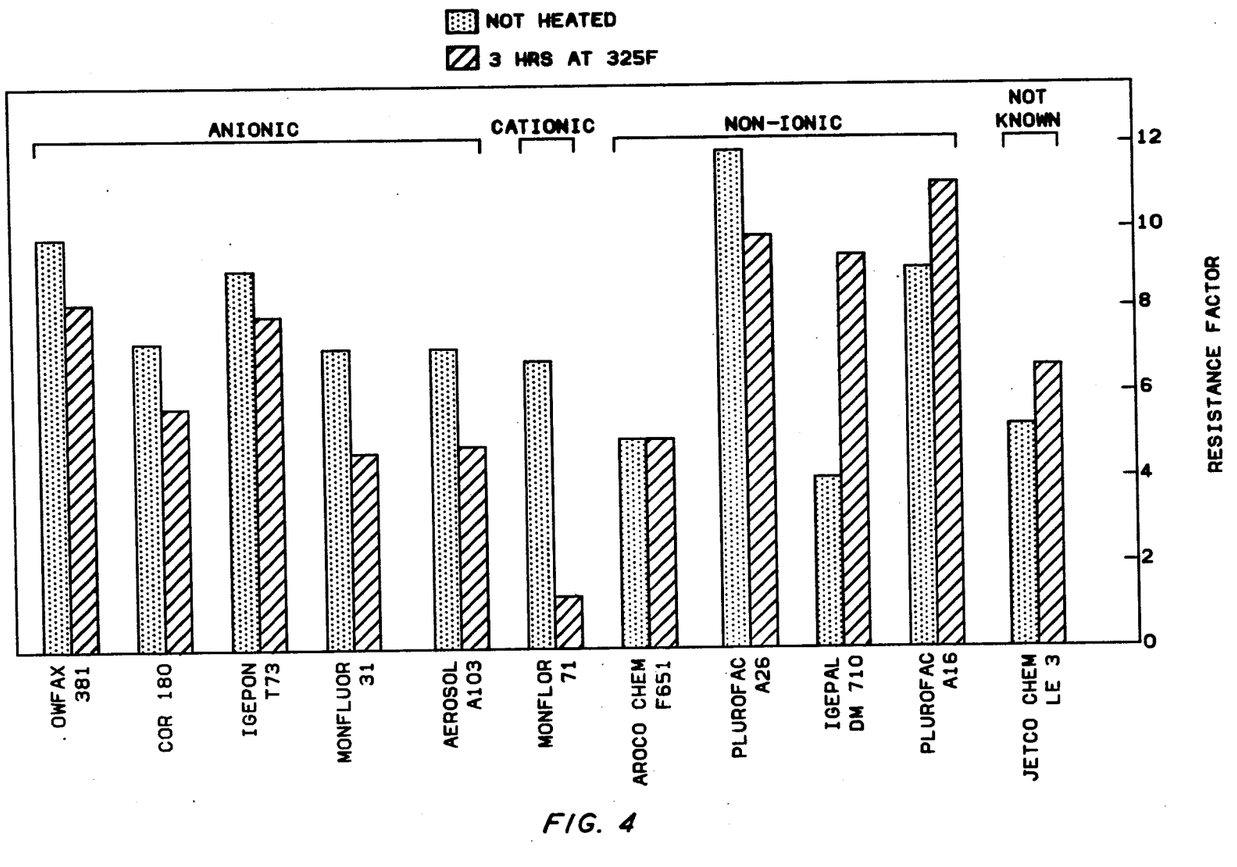
FIG. 4: Graph showing effect of thermal aging on resistance factor.

Thermal stability of a surfactant is also an important consideration in evaluating a surfactant as in field applications the surfactants may be exposed to temperatures of about 300° F. to 500° F. (150°–260° C.). The resistance factor of eleven of the surfactants was evaluated before and after the surfactant solution had been thermally aged at 325° F. (163° C.) for three hours. The results are shown in FIG. 4. In all cases, the resistance factor of the anionic-type surfactants decreased after being thermally aged.

By comparison, the resistance factor of two of the nonionic-type surfactants increased after thermally aging, one remained unchanged, and one decreased. Only one cationic-type surfactant was thermally aged. The resistance factor for this surfactant decreased substantially as a result of thermal aging, and this suggests that cationic-type surfactants may show the same type deterioration as anionic-type surfactants.

Figure 5:
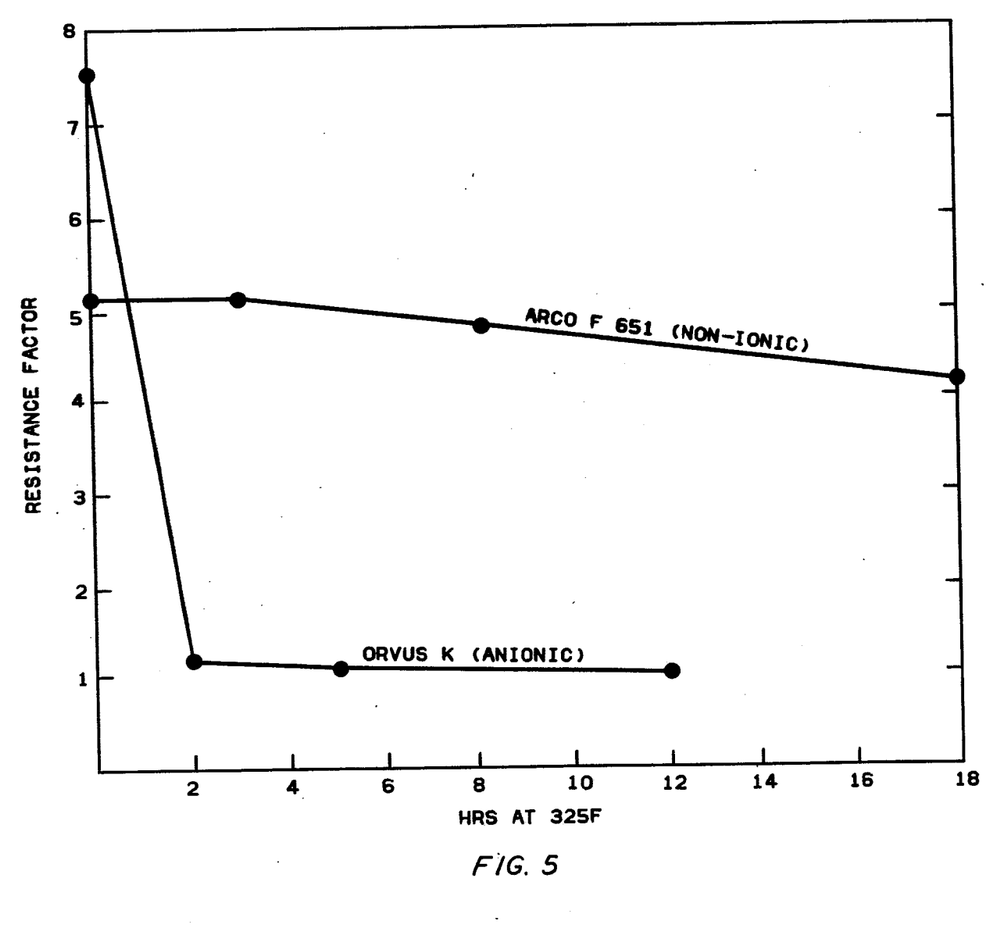
FIG. 5: Graph showing effect of thermal aging on resistance factor; nonionic vs. anionic surfactant solutions.

Thermal aging studies conducted over longer time periods suggest that nonionic surfactants may also thermally degrade and lose their ability to produce foam when exposed to elevated temperature for prolonged periods of time. FIG. 5 shows the resistance factor for nonionic and anionic surfactants that were thermally aged at 325° F. (163° C.) for 18 and 12 hours, respectively. The resistance factor for the nonionic surfactant remained unchanged for three hours and then slowly decreased. After 18 hours, the resistance factor decreased at the rate of about 0.07 units per hour. At that rate of chemical degradation, the ability to divert steam should be completely lost after about 50 hours. The resistance factor of the anionic surfactant deteriorated rapidly, and all ability to stimulate incremental oil production was completely lost after only two hours.

The results of the thermal aging studies suggest that, in field applications, anionic-type surfactants may lose their ability to divert steam two to three hours after being injected into the oil-bearing formation. On the other hand, the ability of nonionic surfactants to divert steam remains unchanged or increases for the first three to four hours and then slowly decreases over the next 50 to 100 hours. These data suggest that nonionic-type surfactants should be preferred for field applications over anionic-type surfactants.

Because Cor 180 has been used most often in field tests, attempts were made to prevent thermal degradation by gelling the surfactant solution with PROD polymer (3,000 ppm $K_2Cr_2O_7 \cdot H_2O$; 4,000 ppm $Na_2S_2O_4$). The results are presented in Table III. The resistance factor was improved by a factor of about two, and the thermal stability was improved substantially by gelling. The results indicate that a PROD-foam system would be a superior system due to its high resistance factor and its impressive thermal stability.

TABLE I

| \multicolumn{4}{c}{Surfactants Evaluated in Example I} | | | |
|---|---|---|---|
| Trade Name | Generic Name | Ionic Name | Supplier |
| Cor 180 | Sulfonated Fatty Acid | Anionic | California Chemical Oil Recovery Company |
| Orvus K | Ammonium Alkyl Sulfonate | Anionic | Proctor and Gamble |
| Igepal CO-210 | Polyethoxylated Hydrophobe | Nonionic | General Aniline & Film |
| Igepal CO-430 | Polyethoxylated Hydrophobe | Nonionic | General Aniline & Film |
| Igepal CO-520 | Polyethoxylated Hydrophobe | Nonionic | General Aniline & Film |
| Igepal DM-530 | Polyethoxylated Hydrophobe | Nonionic | General Aniline & Film |
| Igepal RS-610 | Polyethoxylated Hydrophobe | Nonionic | General Aniline & Film |
| Igepal DM-710 | Polyethoxylated Hydrophobe | Nonionic | General Aniline & Film |
| Igepal CA-720 | Polyethoxylated Hydrophobe | Nonionic | General Aniline & Film |
| Igepal RM-710 | Polyethoxylated Hydrophobe | Nonionic | General Aniline & Film |
| Igepal DM 730 | Polyethoxylated Hydrophobe | Nonionic | General Aniline & Film |
| Igepal DJ-970 | Polyethoxylated Hydrophobe | Nonionic | General Aniline & Film |
| Igepal DM-970 | Polyethoxylated Hydrophobe | Nonionic | General Aniline & Film |
| Igepon T 73 | Na n-methyl-n-oleoyltaurate | Anionic | General Aniline & Film |
| Plurofac A 16 | Oxyethylated S. C. alcohol | Nonionic | Wyandotte Chemical Co. |
| Plurofac A 26 | Oxyethylated S. C. alcohol | Nonionic | Wyandotte Chemical Co. |
| Amoco Well Oil 622 | Composition not available | Nonionic | Amoco Chemicals, Inc. |
| Jetco Chem LE 3 | Composition not available | Nonionic | Jetco Chemical |
| Jetco Chem LE 4 | Composition not available | Nonionic | Jetco Chemical |
| Monflor 31 | $(C_2F_4)_n$ | Nonionic | International Chem., Inc. |
| Monflor 71 | $(C_2F_4)_n$ | Cationic | International Chem., Inc. |
| Haliburton HLX 181 | Soluble Fluorocarbon | — | Haliburton |
| Arco Chem F 651 | Ethoxylated Phenol | Nonionic | Arco Chemical Co. |
| Blancol N | Na salt sulfonated naphthalene-formaldehyde | Anionic | General Aniline & Film |
| BL 330 Antarox | Linear aliphatic | Anionic | General Aniline & Film |
| BL 344 | Polyether | Anionic | General Aniline & Film |
| Pluronics L 31 | Condensate of ethylene oxide with propylene | Nonionic | Wyandotte Chemical Co. |
| Pluronics L 64 | Condensate of ethylene oxide with propylene | Nonionic | Wyandotte Chemical Co. |
| Pluronics F 68 | Condensate of ethylene oxide with propylene | Nonionic | Wyandotte Chemical Co. |
| Pluronics L 81 | Condensate of ethylene oxide with propylene | Nonionic | Wyandotte Chemical Co. |
| Pluronics L 101 | Condensate of ethylene oxide with propylene | Nonionic | Wyandotte Chemical Co. |
| Tetronics 304 | Condensate propylene oxide & ethylene diamine | Nonionic | Wyandotte Chemical Co. |
| Tetronics 904 | Condensate propylene oxide & ethylene diamine | Nonionic | Wyandotte Chemical Co. |
| Aerosol A-101 | | Nonionic | Dow Chemical Company |
| Aerosol A-102 | Alcohol half ester of | Nonionic | Dow Chemical Company |
| Aerosol A-103 | sulfo succinic acid | Nonionic | Dow Chemical Company |
| Dowfax 2 Al | Na dodecyl diphenyl | Nonionic | Dow Chemical Company |
| Dowfax 3 Bl | ether disulfonate | Nonionic | Dow Chemical Company |

TABLE II

Resistance Factor for 38 Surfactants at Room Temperature

| Trade Name | Resistance Factor | Trade Name | Resistance Factor |
|---|---|---|---|
| Plurofac A26 | 11.9 | Bl 344 Antarox | 6.4 |
| Dowfax 2A1 | 10.4 | Orvus K | 6.2 |
| Plurofac A16 | 10.0 | Jetco Chem LE 3 | 5.1 |
| Dowfax 3B1 | 10.0 | BL 330 Antarox | 5.0 |
| Igepal DM 970 | 9.8 | Igepal DM 710 | 4.1 |
| Tetronics 904 | 9.3 | Pluronics L101 | 2.3 |
| Igepal DM 730 | 9.2 | Igepal RS 610 | 2.0 |
| Igepal CA 720 | 8.7 | Igepal CO 520 | 1.3 |
| Aerosol A 102 | 8.5 | Igepal DM 530 | 1.3 |
| Pluronics F 68 | 8.3 | Blancol N | 1.3 |
| Igepal RM 710 | 7.4 | Pluronics L 64 | 1.3 |
| Igepal DJ 970 | 7.3 | Tetronics 304 | 1.3 |
| Monflor 31 | 7.3 | Pluronics L 31 | 1.2 |
| Aerosol A-103 | 7.3 | Jetco Chem LE 4 | 1.2 |
| Cor 180 | 7.2 | Igepal CO 210 | 1.0 |
| Monfluor 71 | 7.1 | Igepal CO 430 | 1.0 |
| Arco Chem E 651 | 6.7 | Amoco Well Oil 622 | 1.0 |
| Aerosol A-101 | 6.6 | Haliburton HLX 181 | 1.0 |
| Igepon T73 | 9.2 | Pluronics L 81 | 1.0 |

TABLE III

Thermal Stability of Surfactant Solutions made with PROD Gels

| | Resistance Factor | |
|---|---|---|
| Hours at 325° F. | 3% Solutions of Cor 180 | 3% Solutions of Cor 180 Gelled with PROD |
| 4.8 | 4.9 | 7.7 |

TABLE III-continued
Thermal Stability of Surfactant Solutions made with PROD Gels

| Hours at 325° F. | Resistance Factor | |
|---|---|---|
| | 3% Solutions of Cor 180 | 3% Solutions of Cor 180 Gelled with PROD |
| 4.9 | 9.3 | * |
| 7.8 | — | 6.5 |
| 8.8 | — | 7.7 |
| 9.0 | 1.2 | 5.7 |

*Remained gelled.

EXAMPLE II

This example, which is taken from copending application Ser. No. 725,305, filed Sept. 21, 1976, exemplifies the "continuous flow-type test" in which the pressure drop is measured across a sand pack during the continuous flow of both a gas and water and then during the continuous flow of both gas and surfactant solution. The continuous method has the advantage over the batch method in that the continuous method allows one to change the concentration of the surfactant while testing since the surfactant solution is continuously being pumped through the sand pack during the test instead of just filling the sand pack with surfactant solution and then displacing with gas.

The relationship between permeability and surfactant effectiveness is also explored in this example.

The foam tests were made by charging fresh water solutions of disodium ethoxylated nonyl phenol half ester of sulfosuccinic acid, supplied by American Cyanamide Company as their Aerosal A103, to sand packs contained in a steel cell. The cell, of schedule 40 pipe, was 2.7 cm in diameter and 29.2 cm in length. Provisions were made to introduce nitrogen gas into the flowing liquid stream before the mix entered the bottom of the sand pack. All the tests reported herein were made with liquid flow rates of 220 cc/hr, and the nitrogen or $CO_2$ (one run) was 2100 cc/hr. A small volume Milton Ray Duplex pump was used in the tests, one cylinder pumping water and the other the surfactant solution. Four channels of a Gulton recorder having transducer ranges of 0-10, 0-50, 0-100, and 0-200 psi were used to monitor pressure drop across the sand pack. Nitrogen or $CO_2$ (one run using $CO_2$) was supplied from cylinders of the compressed gases through regulators and a rotameter with fine needle valve control. Gas pressure on the system was limited to 200 psi because of limitation of rotameter construction. The one $CO_2$ test reported was made at 60 psi.

Test Procedure

1. Pack tube with sand using an electric vibrator to settle the sand. Tube was supported in a vertical position during test.
2. Connect pumping systems to bottom of tube, fill pack with water, and measure pack permeability.
3. Start full flow of water, 220 cc/hr., using both pumps, and measure pressure drop; introduce 2100 cc $N_2$/hr., and measure pressure drop; connect surfactant side of pump to surfactant supply and finally measure pressure drop after maximum foam generation has been reached, indicated by maximum pressure drop across tube. Resistance factor is defined as the $$\frac{\Delta P \text{ for surfactant} + N_2}{\Delta P \text{ for water} + N_2}.$$

Surfactant solution is prepared to make 110 cc with enough surfactant to yield desired concentration in total pump discharge of 220 cc.

4. Complete test, using transducers of the proper pressure range. As the pressure drop increases, the low range transducers are removed from the system to prevent overrange damage.
5. At test conclusion, test lines were flushed before proceeding with the next test.

Results

Test data are summarized below in Table IV. Resistance factors, sand pack permeability, and sand identity are presented. A greater than (>) sign indicates that the nitrogen flow was completely blocked for that test and the numerical value is maximum pressure (200 psi) divided by pressure drop for water-nitrogen flow. It was necessary to use sands with a range of permeabilities (different sands) in order to cover desired range of surfactant. Permeability is determined by Darcy's equation (see U.S. Pat. No. 3,727,687, column 13) wherein K is calculated.

In Table IV, resistance factors for various concentrations of surfactant A-103 in Bartlesville, Okla. tap water and sand packs of different sands having different permeabilities; 220 cc/hr liquid flow; and 2100 cc/hr $N_2$ gas flow have been determined.

TABLE IV

| Test Number | Sand in Pack | % A103 Surfactant in Water | Permeability K in Darcys Before Tests | Resistance Factor |
|---|---|---|---|---|
| TABLE A: | | | | |
| 1 | Mill Creek | 2 | 2.2 | 4.20 |
| 2 | Mill Creek | 2 | 4.2 | 1.49 |
| 3 | Mill Creek | 4 | 5.1 | 1.10 |
| 4 | Mill Creek | 4 | 5.1 | 1.68 |
| 5 | Mill Creek | 4 | 3.0 | >37.0 |
| 6 | Mill Creek | 6 | 4.2 | 8.6 |
| 7 | Mill Creek | 6 | 3.0 | >33 |
| 8[a] | Mill Creek | 6 | 6.2 | >89 |
| TABLE B: | | | | |
| 9 | Ottawa | 4 | 24.0 | 2.0 |
| 10 | Ottawa | 8 | 16.0 | 71.0 |
| 11 | Ottawa | 10 | 16.0 | 113.0 |
| TABLE C: | | | | |
| 12[b] | Nacotoch Outcrop Sand | 2 | 7.4 | 1.6 |

[a] >60 mesh fraction used (>60 cut retained on screen, below 60 passes through screen).
[b] Test made using $CO_2$ as the gas instead of nitrogen.

The resistance factor as defined herein, developed by a surfactant-stabilized foam flowing through a porous media, is found to be dependent upon surfactant concentration and media permeability. At a constant rate of liquid and gas flow, higher resistance factors will be developed in packs of lower permeability. Under the same flow conditions, a large bubbled foam is generated with low surfactant concentrations and high permeability. Smaller bubbled foams with higher resistance factors may be generated in packs of high permeability by increasing surfactant concentration.

Referring to Table IV, for a given concentration of surfactant, say, 2 percent, as the permeability increases from 2.2 Darcys to 4.2 Darcys, the data from the sand pack tests show the resistance factor decreases from 4.2 to 1.49, as shown in Table A. In the three to five Darcy permeability region, the resistance factor decreased from >37 in a 3 Darcy sand pack to about 1.5 Darcys when using 4 percent of A103 surfactant in the water solution in a Mill Creek sand pack. This shows the effect of permeability.

At a given permeability, the data show that when the concentration of the surfactant is increased the resistance factor becomes greater. This is due to a combination of factors, such as an increase in the film toughness, film viscosity, and a reduced liquid drainage rate on the surface of the foam bubbles. This points out that in any reservoir it is necessary to conduct laboratory tests to locate the optimum concentration of surfactant in the liquid solution which would produce a resistance factor of at least 5.

In situ foam diversion projects where the resistance factors are between 1 and 2 will probably be unsuccessful. Resistance factors of the order of 1 to 2 suggests the foam has either collapsed or has insufficient toughness and strength, and in a real situation it would be an ineffective diversion system. The level of resistance factor is readily known to be directly relatable to the effective mobility of fluids in a porous media.

Certain modifications and variations of the invention will become apparent to those skilled in the art, and the illustrative details enclosed are not to be construed as imposing unnecessary limitations on the invention.

I claim:

1. A method for obtaining a measure of foam quality of foam-producing surfactants comprising the steps of:
   (a) filling a sand pack with water;
   (b) displacing the water out of the sand pack by gas flow;
   (c) measuring the pressure drop across the sand pack during the water displacement by the gas flood;
   (d) introducing a surfactant solution into the sand pack;
   (e) displacing the surfactant solution by gas flow;
   (f) measuring the pressure drop across the sand pack during the water displacement by the gas flood; and
   (g) determining the ratio of the maximum differential pressure observed during the surfactant-gas flood to the maximum differential pressure observed during the water-gas flood.

2. A method for evaluating foam-producing surfactants comprising the steps of:
   (a) passing a continuous flow of water and a gas through a sand pack;
   (b) measuring the pressure drop across the sand pack during the continuous flow of both the water and gas; then
   (c) passing a continuous flow of surfactant solution and gas through said sand pack;
   (d) measuring the maximum pressure drop across the sand pack after maximum foam generation has been reached during the continuous flow of both the surfactant solution and gas; and
   (e) determining the ratio of the maximum pressure drop observed during the flow of both the surfactant and gas to the maximum differential pressure observed during the flow of water and gas.

3. A process as in claim 1 wherein said sand pack is in a vertical position and said gas is $N_2$ or $CO_2$.

4. A process as in claim 2 wherein said sand pack is in a vertical position and said gas is $N_2$ or $CO_2$.

5. A process as in claim 1 wherein steps (a) through (g) are repeated on the surfactant solution after the surfactant solution is heated at a temperature in the range of about 300°–500° F. (150°–260° C.) for a period of time up to about 100 hours.

6. A process as in claim 5 wherein said temperature is about 325° F. (163° C.) and said period of time is in the range of about 3–18 hours.

7. A process as in claim 2 wherein steps (a) through (e) are repeated on the surfactant solution after the surfactant solution is heated at a temperature in the range of about 300°–500° F. (150°–260° C.) for a period of time up to about 100 hours.

8. A process as in claim 7 wherein said temperature is about 325° F. (163° C.) and said period of time is in the range of about 3–18 hours.

9. A process as in claim 2 wherein the flow rate of said gas is about 220 cc/hr and the flow rate of said surfactant solution or water is 2100 cc/hr and the permeability of the sand pack is determined.

10. A process as in claim 1 wherein steps (a) through (g) are repeated after the surfactant solution is heated at a temperature for a length of time approximating the condition of temperature the surfactant will be exposed to in the field application.

11. A process as in claim 2 wherein steps (a) through (e) are repeated after the surfactant solution is heated at a temperature for a length of time approximating the condition of temperature the surfactant will be exposed to in the field application.

12. A method for evaluating foam-producing surfactants to be used in secondary oil recovery methods by comparing the maximum differential pressure observed across a sand pack during displacement of water from said sand pack with a gas to the maximum differential pressure observed across said sand pack during displacement of the surfactant from said sand pack by said gas.

* * * * *